(12) United States Patent
Asirvatham et al.

(10) Patent No.: US 12,414,789 B2
(45) Date of Patent: Sep. 16, 2025

(54) PERICARDIAL MODIFICATION SYSTEMS AND METHODS FOR HEART FAILURE TREATMENT

(71) Applicant: Mayo Foundation for Medical Education and Research, Rochester, MN (US)

(72) Inventors: Samuel J. Asirvatham, Rochester, MN (US); Barry A. Borlaug, Rochester, MN (US); Vojtech Melenovsky, Prague (CZ)

(73) Assignee: Mayo Foundation for Medical Education and Research, Rochester, MN (US)

( * ) Notice: Subject to any disclaimer, the term of this patent is extended or adjusted under 35 U.S.C. 154(b) by 361 days.

(21) Appl. No.: 18/109,650

(22) Filed: Feb. 14, 2023

(65) Prior Publication Data

US 2023/0181208 A1    Jun. 15, 2023

Related U.S. Application Data

(63) Continuation of application No. 16/793,399, filed on Feb. 18, 2020, now Pat. No. 11,612,405, which is a
(Continued)

(51) Int. Cl.
*A61B 17/295* (2006.01)
*A61B 17/29* (2006.01)
(Continued)

(52) U.S. Cl.
CPC ............ *A61B 17/295* (2013.01); *A61B 17/29* (2013.01); *A61B 17/320016* (2013.01);
(Continued)

(58) Field of Classification Search
CPC .................. A61B 17/295; A61B 17/29; A61B 17/320016; A61B 17/3201;
(Continued)

(56) References Cited

U.S. PATENT DOCUMENTS

| | | | |
|---|---|---|---|
| 5,931,810 A | 8/1999 | Grabek | |
| 6,231,518 B1 * | 5/2001 | Grabek | A61B 90/36 |
| | | | 600/508 |

(Continued)

FOREIGN PATENT DOCUMENTS

| | | |
|---|---|---|
| JP | 2002-113009 | 4/2002 |
| JP | 2007-509702 | 4/2007 |

(Continued)

OTHER PUBLICATIONS

Belenkie et al., "Ventricular interaction: from bench to bedside," Ann Med., 33(4):236-241, May 2001.
(Continued)

*Primary Examiner* — Brooke Labranche
(74) *Attorney, Agent, or Firm* — Fish & Richardson P.C.

(57) ABSTRACT

This document relates to devices and methods for the treatment of heart conditions. For example, this document provides devices and methods for treating heart failure with preserved ejection fraction, including diastolic heart failure, by performing a pericardial modification procedure.

18 Claims, 7 Drawing Sheets

Related U.S. Application Data continuation of application No. 16/406,983, filed on May 8, 2019, now Pat. No. 10,603,062, which is a continuation of application No. 14/773,487, filed as application No. PCT/US2014/023081 on Mar. 11, 2014, now Pat. No. 10,307,179.

(60) Provisional application No. 61/798,382, filed on Mar. 15, 2013, provisional application No. 61/776,483, filed on Mar. 11, 2013.

(51) Int. Cl.
| | | |
|---|---|---|
| *A61B 17/32* | (2006.01) | |
| *A61B 17/3201* | (2006.01) | |
| *A61B 17/3205* | (2006.01) | |
| *A61B 17/3209* | (2006.01) | |
| *A61B 17/00* | (2006.01) | |
| *A61B 17/22* | (2006.01) | |
| *A61B 18/00* | (2006.01) | |
| *A61B 18/14* | (2006.01) | |

(52) U.S. Cl.
CPC .... *A61B 17/3201* (2013.01); *A61B 17/32053* (2013.01); *A61B 17/3209* (2013.01); *A61B 2017/00225* (2013.01); *A61B 2017/00247* (2013.01); *A61B 2017/003* (2013.01); *A61B 2017/00318* (2013.01); *A61B 2017/22039* (2013.01); *A61B 2017/2906* (2013.01); *A61B 2018/00595* (2013.01); *A61B 2018/00839* (2013.01); *A61B 18/1445* (2013.01); *A61B 18/1492* (2013.01)

(58) Field of Classification Search
CPC .......... A61B 17/32053; A61B 17/3209; A61B 18/1445; A61B 18/1492; A61B 2017/00247

See application file for complete search history.

(56) References Cited

U.S. PATENT DOCUMENTS

| | | | |
|---|---|---|---|
| 6,478,028 | B1 | 11/2002 | Paolitto et al. |
| 6,585,635 | B1 | 7/2003 | Aldrich |
| 6,599,526 | B2 | 7/2003 | Dimitrijevich |
| 7,226,440 | B2 | 6/2007 | Gelfand et al. |
| 7,270,669 | B1 | 9/2007 | Sra |
| 7,331,972 | B1 | 2/2008 | Cox |
| 7,398,781 | B1 | 7/2008 | Chin |
| 8,545,387 | B2 | 10/2013 | Harrison et al. |
| 8,652,025 | B2 | 2/2014 | Laufer et al. |
| 8,986,278 | B2 | 3/2015 | Fung et al. |
| 9,173,705 | B2 | 11/2015 | Whayne et al. |
| 9,220,490 | B2 | 12/2015 | Guenst |
| 10,098,695 | B2 | 10/2018 | Asirvatham et al. |
| 10,307,179 | B2 | 6/2019 | Asirvatham et al. |
| 10,603,062 | B2 | 3/2020 | Asirvatham et al. |
| 2002/0107514 | A1 | 8/2002 | Hooven |
| 2003/0009145 | A1 | 1/2003 | Struijker-Boudier et al. |
| 2003/0060415 | A1 | 3/2003 | Hung |
| 2004/0102804 | A1 | 5/2004 | Chin |
| 2004/0138527 | A1 | 7/2004 | Bonner |
| 2004/0167558 | A1* | 8/2004 | Igo ............... A61B 17/3478 606/185 |
| 2006/0173441 | A1 | 8/2006 | Gelfand et al. |
| 2006/0247672 | A1 | 11/2006 | Vidlund |
| 2007/0083082 | A1 | 4/2007 | Kiser |
| 2010/0063475 | A1 | 3/2010 | Jahns |
| 2010/0234827 | A1 | 9/2010 | Sigg et al. |
| 2011/0112569 | A1 | 5/2011 | Friedman |
| 2011/0218528 | A1 | 9/2011 | Ogata et al. |
| 2012/0191090 | A1 | 7/2012 | Sugahara et al. |
| 2012/0296153 | A1 | 11/2012 | Laufer et al. |
| 2013/0046305 | A1 | 2/2013 | Davies et al. |
| 2014/0053111 | A1 | 2/2014 | Beckman |
| 2014/0330263 | A1 | 11/2014 | De Canniere |
| 2015/0265304 | A1 | 9/2015 | Feldman et al. |
| 2015/0313634 | A1 | 11/2015 | Gross et al. |
| 2016/0015410 | A1 | 1/2016 | Asirvatham et al. |
| 2016/0058504 | A1 | 3/2016 | Davies et al. |
| 2017/0258521 | A1 | 9/2017 | Asirvatham et al. |

FOREIGN PATENT DOCUMENTS

| | | |
|---|---|---|
| JP | 2007-181696 | 7/2007 |
| JP | 2010-508959 | 3/2010 |
| WO | WO 2005/044079 | 5/2005 |
| WO | WO 2008/057117 | 5/2008 |
| WO | WO 2011/130456 | 10/2011 |
| WO | WO 2014/164641 | 10/2014 |

OTHER PUBLICATIONS

Bhargava et al., "Influence of the pericardium on left ventricular diastolic pressure-volume curves in dogs with sustained volume overload," Am Heart J., 105(6):995-1001, Jun. 1983.

Crawford et al., "Effect of the undisturbed pericardium on left ventricular size and performance during acute volume loading," Am Heart J., 105(2):267-272, Feb. 1983.

European Office Action in International Application No. EP 14778493.8, dated Aug. 8, 2018, 4 pages.

European Search Report for Application No. 14778493.8, dated Sep. 30, 2016, 8 pages.

Hammond et al., "Heart size and maximal cardiac output are limited by the pericardium," Am J Physiol., 263(6 Pt 2):H1675-H1681, Dec. 1992.

International Preliminary Report on Patentability for PCT/US2014/02081, mailed Sep. 24, 2015, 8 pages.

International Search Report and Written Opinion for PCT/US2014/023081, mailed Jul. 9, 2014, 13 pages.

International Search Report and Written Opinion for PCT/US2017/21512, mailed May 31, 2017, 12 pages.

Japanese Office Action in International Application No. JP2016-501148, issued Dec. 20, 2017, (10 pages including English Translation).

Spadaro et al., "Pericardial modulation of right and left ventricular diastolic interaction," Circ Res., 48(2):233-238, Feb. 1981.

Stray-Gundersen et al., "The effect of pericardiectomy on maximal oxygen consumption and maximal cardiac output in untrained dogs," Circ Res., 58(4):523-530, Apr. 1986.

U.S. Appl. No. 15/356,200, filed Nov. 18, 2016, Samuel J. Asirvatham.

* cited by examiner

PERICARDIAL MODIFICATION SYSTEMS AND METHODS FOR HEART FAILURE TREATMENT

CROSS-REFERENCE TO RELATED APPLICATIONS

This application is a continuation of U.S. application Ser. No. 16/793,399, filed Feb. 18, 2020, which is a continuation application of U.S. application Ser. No. 16/406,983 (now U.S. Pat. No. 10,603,062), filed May 8, 2019, which is a continuation application of U.S. application Ser. No. 14/773,487 (now U.S. Pat. No. 10,307,179), filed Sep. 8, 2015, which is a National Stage application under 35 U.S.C. § 371 of International Application No. PCT/US2014/023081, filed Mar. 11, 2014, which claims the benefit of U.S. Provisional Application Ser. No. 61/798,382, filed Mar. 15, 2013, and U.S. Provisional Application Ser. No. 61/776,483, filed Mar. 11, 2013. The disclosure of the prior applications are considered part of (and are incorporated by reference in) the disclosure of this application.

BACKGROUND

1. Technical Field

This document relates to devices and methods for the treatment of heart conditions. For example, this document relates to devices and methods for treating heart failure with preserved ejection fraction, including diastolic heart failure, by performing a pericardial modification procedure.

2. Background Information

The pericardium is the thin double-layered fluid filled sac that surrounds the heart and the roots of the aorta, vena cava, and the pulmonary artery. The outer sac is known as the fibrous pericardium. The inner sac is known as the serous pericardium. The serous pericardium consists of a visceral layer portion and a parietal layer portion ("parietal pericardium"). The visceral layer, or epicardium, covers the heart and the great vessels. The parietal portion lines the outer fibrous pericardium.

The phrenic nerves run from the brain to the diaphragm. The phrenic nerves provide motor impulses to muscles of the diaphragm, thereby causing breathing. The right phrenic nerve passes underneath the muscles of the neck and bones of the shoulder to the base of the right lung, contacting the heart and the windpipe. The left nerve follows a similar path, passing close to the heart before entering the diaphragm.

SUMMARY

This document provides devices and methods for the treatment of heart conditions. For example, this document provides devices and methods for treating heart failure with preserved ejection fraction, including diastolic heart failure, by performing a pericardial modification procedure.

In general, one aspect of this document features a method for treating diastolic heart failure. The method comprises creating a tent of pericardial tissue on a heart of a patient, wherein said tent is created using a grasping device; creating an opening in said pericardial tissue, wherein said opening is created using a cutting device to cut or puncture a portion of said tent of pericardial tissue; and relieving pressure exerted by said pericardial tissue on said heart as a result of creating said opening.

In some implementations said method for treating diastolic heart failure may be performed percutaneously. Said grasping device and said cutting device may be catheter-based devices. Said grasping device and said cutting device may comprise a single catheter-based device. Said method may further comprise probing to ascertain a location of a phrenic nerve. At least a portion of said pericardial tissue may be removed from said patient.

In general, another aspect this document features a method for treating diastolic heart failure. Said method comprises: identifying a patient having diastolic heart failure; and creating an opening in said patient's pericardial tissue or removing a portion of said patient's pericardial tissue, wherein said creating or said removing reduces pressure exerted by said pericardial tissue on said patient's heart.

In some implementations said method for treating diastolic heart failure may further comprise probing to ascertain a location of a phrenic nerve.

Particular embodiments of the subject matter described in this document can be implemented to realize one or more of the following advantages. In some embodiments, heart conditions such as diastolic heart failure and others can be treated using the devices and methods provided herein. In some embodiments, various heart conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1A:
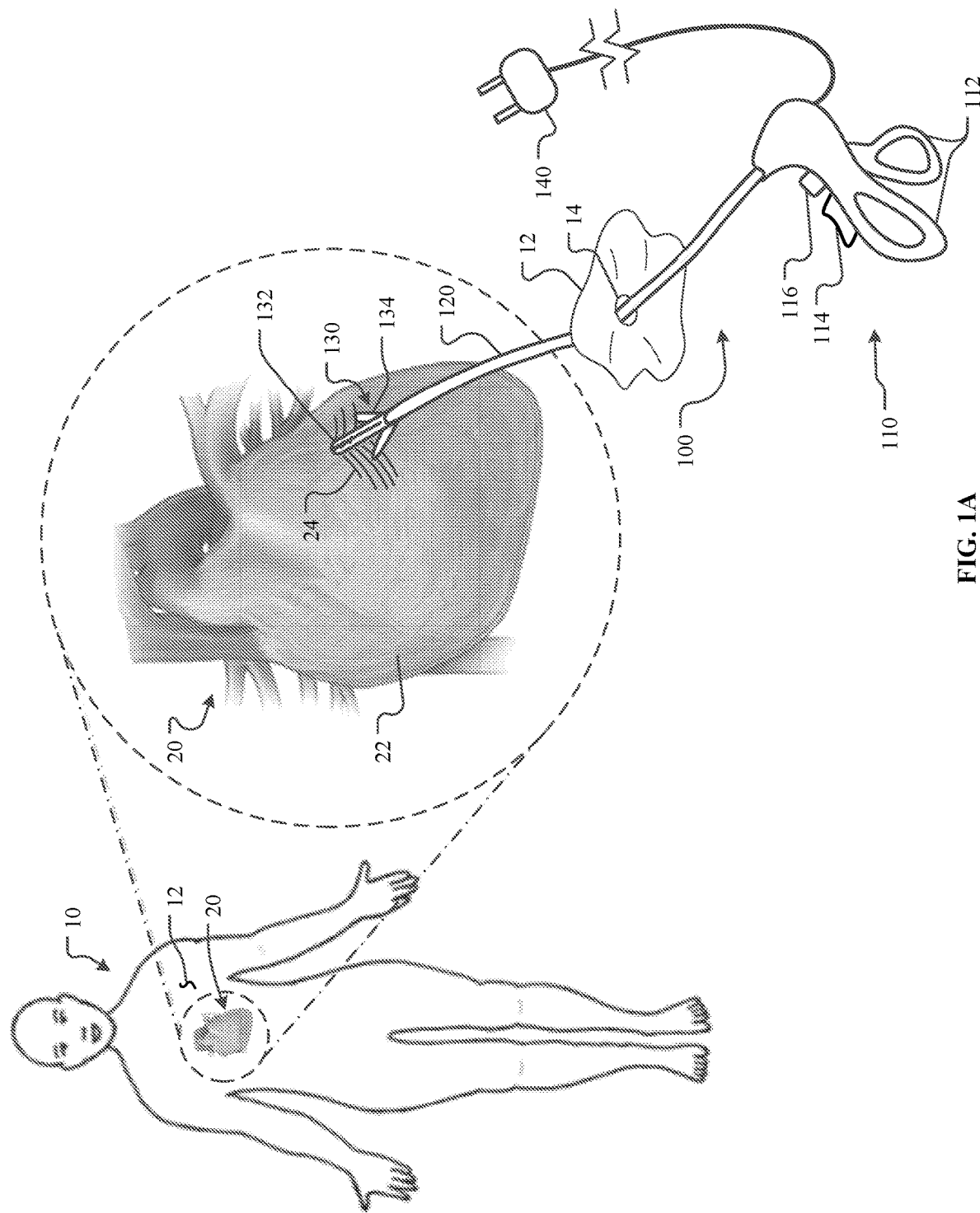
FIG. 1A is a schematic diagram of patient undergoing a pericardectomy using an exemplary catheter-based pericardectomy device system in accordance with some embodiments provided herein.

This document provides devices and methods for the treatment of heart conditions. For example, this document provides devices and methods for treating heart failure with preserved ejection fraction (HFpEF), including diastolic heart failure, by performing a pericardial modification procedure. The devices and methods provided herein may also be used to treat other conditions for which pericardial modifications, including but not limited to removal of all or part of the pericardium, are advantageous. In some implementations, the devices and methods provided herein may be used to treat conditions such as increased diastolic ventricular interaction, pulmonary arterial hypertension, and right ventricular myocardial infarction, to provide some additional examples.

The devices and methods provided herein can also be used to treat pericardium disorders (e.g., pericarditis, pericardial effusion, etc.). In addition, the devices and methods provided herein can also be used on pericardial sacs that are themselves healthy—so as to treat other related conditions, such as HFpFE, including diastolic heart failure.

As used within this document, the term "parietal pericardium," when used in the context of incising, dilating, removing, or otherwise modifying all or portions thereof, is defined to include a corresponding portion of fibrous pericardium. For example, the removal of a strip of parietal pericardium by definition also includes the removal of a corresponding strip of fibrous pericardium.

In some embodiments using devices and methods provided herein, HFpFE is treated by performing a full pericardectomy. In some embodiments, the treatment performed is a partial pericardectomy. In some embodiments, no pericardial tissue is removed, but the pericardial tissue is modulated or otherwise modified in such a way as to remove the constrictive force of the pericardial sac on the heart. For example, in some embodiments, a strip of the parietal pericardium is removed by cutting, tearing, slitting, expanding, cauterizing, and the like. In some embodiments, holes or tears are made in the pericardial sac, thereby facilitating dilation of the pericardium. In some embodiments the pericardial sac is slit, expanded, torn, cauterized, cut, or in some other fashion modulated or modified, to remove the constrictive force of the pericardial sac on the heart.

In some embodiments, only the outer parietal pericardium is modified, modulated, or fully or partially removed. In some embodiments, both the parietal and the visceral layers of pericardium are modified, modulated, or fully or partially removed. In some embodiments, the parietal layer is fully removed and the visceral layer is modified, modulated, or partially removed.

In some cases, the visceral layer of pericardium can be modified, modulated, or fully or partially removed with or without modifying, modulating, or fully or partially removing the outer parietal pericardium. For example, the visceral layer of pericardium can be modified or modulated by using DC/RF to soften of the visceral layer.

In some embodiments, the phrenic nerves are detached from the parietal pericardium as part of the pericardial modification procedure. In some embodiments, the phrenic nerves are left attached to a portion of the parietal pericardium that is left remaining on the heart while other portions of the parietal pericardium are removed.

The devices and methods for pericardial modification provided herein encompass a range of surgical devices and techniques. In some embodiments, the pericardial modification is performed percutaneously. The approach can be, for example, subxiphoidal or lateral or via thoracotomy. In some cases it may be possible to perform the procedure by entering the heart and puncturing out of the heart through a myocardial wall (e.g. ventricle, atrium, appendage, etc.) to gain access to the pericardial space (e.g., an inside-out approach). In some embodiments, video-assisted thoracoscopy can be used. In some embodiments, robotic assistance can be used. In some embodiments, open-chest techniques are used. In some embodiments, a combination of such techniques are used.

In some embodiments, cutting of the pericardium is performed from the outside of the pericardium. In some embodiments, the pericardial sac is initially punctured by a device, and then the cutting is performed from within the pericardial space in a direction generally outward from heart tissue.

Devices having a variety of functional features are used to perform the pericardial modification methods provided herein. In some embodiments, the devices provided herein are flexible catheter-based grasping devices (e.g., forceps, suction devices, cryo/cooling devices, and/or snares). In some embodiments, the devices provided herein are flexible catheter-based cutting devices (e.g., scissors, sheaths, knife, scapel, lasers, snares, cryogenic devices, and electrocautery devices). In some embodiments, the grasping and cutting devices are combined on a single catheter device. In some embodiments, the grasping and cutting devices are separate devices. In some embodiments, the catheter-based devices provided herein can install hooks, anchors, and/or clips in a temporary manner to assist with performing the pericardectomy techniques. In some embodiments, an expandable element (e.g., a balloon, nitinol-based devices, etc.) can be used to create a working space in the pericardial sac and to protect the heart or otherwise direct the cutting instrument.

Components for visualizing, probing, and sensing the anatomy may be included with the devices provided herein. For example, in some embodiments the devices provided herein include electrode devices for stimulating or sensing the phrenic nerves. In some embodiments, the devices provided herein include an impedance measurement probe for sensing tissue or nerves. In some embodiments, the devices provided herein include a Doppler probe for visualizing the anatomy. In some embodiments, the devices provided herein include an optical camera for providing images of internal anatomy. In some embodiments, the devices provided herein include thoracoscopy style devices.

Further additional functional features are included in some embodiments of devices provided for performing the pericardial modification methods provided herein. In some embodiments, stabilization devices are included. In some embodiments, balloon devices are included. In some embodiments, opposable catheters with magnetic coupling are included. In some such embodiments, a first catheter can be located within the pericardial space, a second catheter can be located on the exterior of the pericardium, and a magnetic coupling between the two catheters can enable them to cooperatively perform a pericardectomy procedure.

With reference to FIG. 1A, a human patient 10 is depicted as undergoing a pericardectomy procedure using an example pericardectomy device 100. Patient 10 has a skin surface 12, and a heart 20 that is encompassed by a pericardium 22.

Example pericardectomy device 100 is a catheter-based device configured for percutaneous functionality. That is, pericardectomy device 100 is insertable through a skin penetration point 14, such as an incision. In some cases, a trocar device is employed in skin penetration point 14. In some cases, a delivery sheath or endoscope is installed in patient 10 to direct the placement of the pericardectomy device 100.

While pericardectomy device 100 is depicted as a single catheter, in some embodiments two or more catheter-based devices are used to perform the pericardectomy procedures provided herein. In some cases, multiple skin penetration points may be employed. Still further, in some embodiments, an open-chest procedure, or a thoracoscopy procedure can be used to perform the pericardectomy procedures provided herein.

Example pericardectomy device 100 includes an actuator 110, a flexible catheter 120, and an operative distal end 130. In this example, operative end 130 includes a grasping device 132 and a cutting device 134. Example pericardectomy device 100 also includes a bipolar connection 140 for energizing operative end 130.

Some embodiments of the pericardial modification methods provided herein include provisions to avoid or minimize dissection or damage to particular structures such as the phrenic nerves or blood vessels. To facilitate avoidance of damage to structures such as the phrenic nerves, some embodiments of operative end 130 include a device such as an electrode (not shown) that can be used to identify the location of the phrenic nerves. Phrenic nerves control the motor impulses to muscles of the diaphragm. When the electrode is in the proximity of the phrenic nerves, electrical pulses generated from the electrode will stimulate movement of the diaphragm that can be visualized by clinicians. Hence, when electrical pulses delivered by an electrode result in no movement of the diaphragm, it can be determined that the phrenic nerves are not in the immediate vicinity of operative end 130. In such cases, grasping and cutting of the pericardium by operative end 130 can be performed in the immediate vicinity with a low likelihood of incurring damage to the phrenic nerves.

In some cases, to identify and/or avoid damage to the vessels, an algorithm for vessel identification and turning off energy delivery can be used. In some cases, sensors such as Doppler probes or impedance measurements from electrograms can be used. For example, impedance from myocardium and pericardium can stay stable through the cardiac cycle for the most part, but a characteristic phasic variation can occur in any hollow viscus or as a result of change with contact or pressure or internal diameter. This can occur in arteries and can be used identify quickly where arteries are when a device provided herein is placed into position.

In some embodiments, squeezing the two handles 112 together can close the grasping device 132 to secure a portion of the pericardium 22. In some embodiments, grasping device 132 is a forceps, and the jaws of the forceps can be closed by squeezing handles 112 together. In some embodiments, grasping device 132 can perform both grasping and cutting operations. For example, grasping device 132 can be configured to grasp pericardium 22 using an initial amount of clamping force, and by applying a greater amount of force the jaws of grasping device 132 can cut through pericardium 22.

In some embodiments, grasping device 132 is a suction member that can retract pericardium 22. The suction force can be applied to pericardium 22 in a controllable fashion using actuator 110. In some embodiments, other suitable types of grasping devices 132, including cryogenic devices, are included with pericardectomy device 100.

In some embodiments, grasping device 132 is an electrocautery device. In such embodiments, a single grasping device 132 can grasp, sever, and cauterize pericardium 22. Bipolar connection 140 can be connected to an energy source, such as a RF cautery system power supply. The electrocautery operation can be initiated by a clinician operator using actuator 110, such as by pushing a button 116.

In some embodiments, some or all of catheter 120 is steerable. For example, in some embodiments operative end 130 is steerable using actuator 110. In some such embodiments, grasping device 132 can be canted away from heart 20 to create a pericardium tent 24. That is, after grasping device 132 has secured a portion of pericardium 22, the clinician operator of pericardectomy device 100 can steer operative end 130 to pull pericardium 22 away from heart 20 to create a tent-like portion of pericardium 24.

In some embodiments, a balloon device (not shown) can be used to create pericardium tent 24. For example, an un-inflated balloon can be positioned in the pericardial space. Then the balloon can be inflated to create pericardium tent 24. In some embodiments, the inflation of the balloon can be used to expand or tear a hole or incision that was made in the pericardium.

In some embodiments, one side of the balloon device can include one or more RF electrodes. The side of the balloon with the one or more RF electrodes can be positioned abutting the underside of pericardium 22. The RF electrodes can be activated to damage parietal pericardium. Alternately, the orientation of the balloon can be reversed and the RF electrodes can perform ablation of the epicardial pericardium.

Pericardium tent 24 facilitates the isolation of a portion of pericardium 22 so that the cutting of pericardium 22 can occur with less risk of damaging other tissues. In some embodiments, a stabilizing device (not shown) can also be used to reduce movement of pericardium 22 in preparation for cutting.

Cutting device 134 can be located at a position at operative end 130 to cooperate with grasping device 132. For example, in some embodiments, cutting device 134 is locatable between the jaws of grasping device 132. In some embodiments, cutting device 134 is locatable adjacent to grasping device 132. In this manner, cutting device 134 can be in position to cut pericardium tent 24 created by grasping device 132. In some embodiment, cutting device 134 is locatable and maneuverable independent of grasping device 132.

Cutting device 134 can be actuated by a clinician operator using actuator 110. For example, in some embodiments pulling a trigger 114 can operate cutting device 134. In some embodiments after cutting, the exposed edges of pericardium 22 can be cauterized using pericardectomy device 100.

A variety of types of cutting devices 134 can be used. In some embodiments, cutting device 134 is a scissors tool. In some embodiments, cutting device 134 is a scalpel blade. In some embodiments, the tip(s) of cutting device 134 have sharp points. In some embodiments, the tip(s) of cutting device 134 have blunt points. In some embodiments, cutting device 134 is a snare or lasso that can be positionally maneuvered axially and radially on catheter 120. The snare can be used to capture and cinch portions of pericardium tent 24, and then cut it. In some embodiments, the snare can also cauterize pericardium 22. In some embodiments, other suitable types of cutting devices are used on pericardectomy device 100.

In some embodiments, the pericardial sac 22 is initially punctured by a device (e.g., grasping device 132 or cutting device 134), then the cutting is performed from within the pericardial space, and in a direction generally outward and away from heart tissue.

In some embodiments of pericardectomy device 100, two opposing catheters are used. One catheter can have its tip positioned in the pericardial space to create pericardium tent 24. A second catheter can be located external to the pericardial space and can perform grasping/cutting operations on pericardium tent 24. In some embodiments, the opposing catheters are magnetically coupled to each other to coordinate their relative positions in an advantageous manner. In some embodiments, the opposing catheters are mechanically coupled together, or in other suitable manners, to coordinate their relative positions.

After a single cut or multiple cuts to pericardium 22 have been made, pericardectomy device 100 can be repositioned to another area of pericardium 22 as desired. The actions can be repeated to cut (or tear, puncture, dissect, etc.) another portion of pericardium 22. By repeating the actions described herein, pericardium 22 can be removed to the extent desired—which may be a full or partial removal of pericardium 22.

Figure 1B:
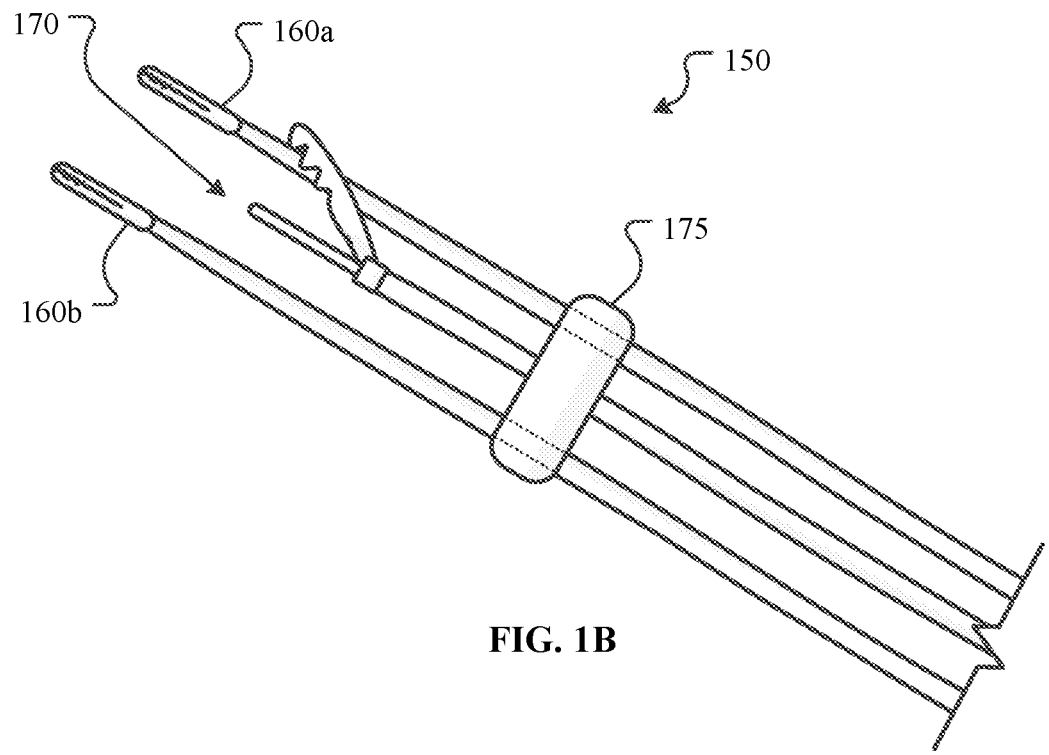
FIGS. 1B and 1C are schematic illustrations of another exemplary pericardectomy device system in accordance with some embodiments provided herein.
Figure 1C:
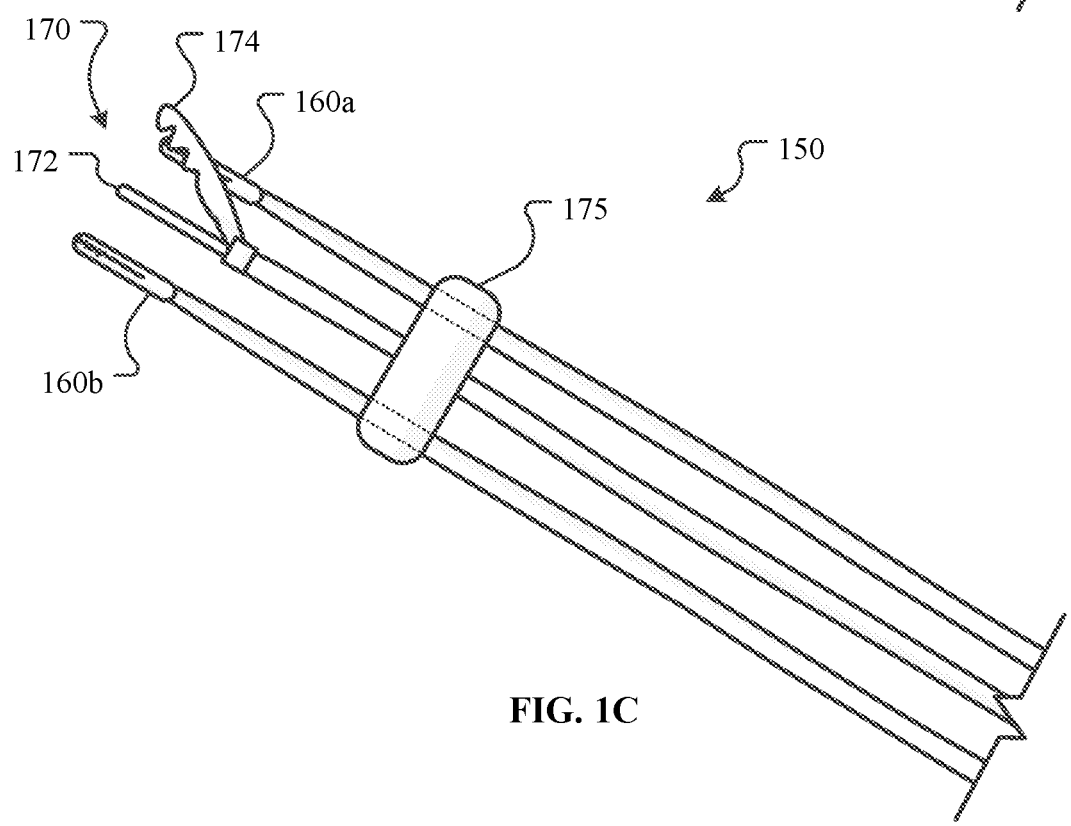

With reference to FIGS. 1B and 1C, another example pericardectomy device 150 is provided. Pericardectomy device 150 includes two graspers 160a and 160b that flank the position of a central electrocautery tissue cutter 170. In some embodiments, the orientation of graspers 160a-b to cutter 170 can be controlled by a coupler 175, or in some embodiments by an over-tube device. In some embodiments, coupler 175 is fixedly coupled to cutter 170 and slidably coupled to graspers 160a-b. In some embodiments, an endoscope and light source are included with pericardectomy device 150. In some embodiments, central electrocautery tissue cutter 170 is also used as a probe that is used to stimulate the phrenic nerve so as to detect and map the location of the phrenic nerves.

In some embodiments, pericardectomy device 150 can include one or more electrodes that can be used to trace electrical potentials on tissues such as the pericardial tissue. In some implementations, such tracing of electrical potentials can be useful for navigation of pericardectomy device 150 within the patient.

In some embodiments, graspers 160a-b are over-the-wire grasping tools. In other words, graspers 160a-b can be installed over a guidewire device. In some embodiments, graspers 160a-b are configured for a monorail-type guidewire system. In some embodiments, graspers 160a-b are configured for a central wire advancement guidewire system. That is, graspers 160a-b can include a longitudinal lumen that can slidably receive a guidewire, or graspers 160a-b can include a collar (e.g., refer to FIGS. 4 and 5) that can slidably receive a guidewire. In some embodiments, only one jaw of graspers 160a-b is pivotable, while the other jaw is fixed. In some embodiments, both jaws of graspers 160a-b are pivotable.

In some embodiments, the longitudinal lumen of graspers 160a-b that are so equipped can be used to convey a contrast media for fluoroscopy. In some such embodiments, the lumen can be confluent with the jaws of graspers 160a-b. When pericardectomy device 150 is in use, the contrast media can be used to visualize that one jaw of graspers 160a-b is above the pericardium and the other jaw is below the pericardium as desired. That is, the jaw beneath the pericardium can be visualized by the contrast media being contained within the pericardial space, and the jaw above the pericardium can be visualized by the contrast media being dispersed outside of the pericardial space. In some embodiments, contract media can be delivered through one to or both graspers 160a-b while graspers 160a-b are engaged with pericardial tissue. This delivery of contrast media can stain the pericardial tissue to enhance the radiographical visualization thereof.

To maneuver pericardectomy device 150 into position near the outer surface of the patient's pericardium, first the guidewire can be percutaneously installed. After installing the guidewire to the pericardial space, a first grasper 160a can be advanced over the guidewire, and the grasper 160a can be clamped onto a portion of pericardium. Then grasper 160a can be detached from the guidewire (assuming a monorail-type guidewire system). The second grasper 160b can then be advanced over the same guidewire, and clamped onto a portion of pericardium adjacent to the other grasper 160a. Then a single overtube device or coupler 175 can be installed onto the shafts of graspers 160a-b. Coupler 175 can include a central cutting tool such as electrocautery tissue cutter 170. Electrocautery tissue cutter 170 can be advanced to the area of graspers 160a-b. Alternatively, in some implementations two or more guidewires can be utilized. In some such implementations, graspers 160a-b and tissue cutter 170 can thereby be advanced over guidewires that are distinct from each other.

The general operation of pericardectomy device 150 can be as follows (this description assumes that pericardectomy device 150 is already within a patient and near the outer surface of the patient's pericardium). A clinician can manipulate graspers 160a-b to advance them beyond cutter 170 as shown in the configuration of FIG. 1B. Graspers 160a-b can slide in relation to coupler 175 (or an overtube device) to thereby advance beyond cutter 170. Graspers 160a-b can be used to grasp or pinch a portion of the pericardium. With portions of pericardial tissue contained within the jaws of graspers 160a-b, a pericardial tent is formed between graspers 160a-b.

Next, cutter 170 can be advanced by the clinician to a location generally adjacent to graspers 160a-b as shown in FIG. 1C. A probe 172 of cutter 170 can puncture the pericardial tent. Then a jaw 174 of cutter 170 can be pivoted by the clinician to come into contact with the pericardial tent. Energy for bi-polar electrocauterization can be delivered to cutter 170 to sever and cauterized the pericardial tissue contained between probe 172 and jaw 174. After the cutting, the clinician can open the jaws of graspers 160a-b, and then advance graspers 160a-b to the next desired location to be cut. The configuration of pericardectomy device 150 can then once again resemble FIG. 1B. The process steps above can be repeated until the pericardial cutting is completed to the extent desired.

After completion of the cutting process, or at one or more times during the cutting process, portions of pericardial tissue can be severed and removed from the patient. This severing and removal of the pericardial tissue can be performed using various techniques. In one example, a bipolar snare tool (not shown, but similar to those devices used for removing polyps) can be advanced over graspers 160a-b while graspers 160a-b are holding pericardial tissue. The bipolar snare tool can be advanced beyond the distal end of graspers 160a-b and into contact with the pericardial tissue. The bipolar snare tool can be activated while the graspers 160*a-b* continue to hold the pericardial tissue. After the energy from bipolar snare tool has severed a portion of the pericardial tissue, graspers 160*a-b* can be withdrawn from the patient while the portion of the pericardial tissue is in the jaws of graspers 160*a-b*.

FIGS. 2A-2D illustrate various example partial pericardium 22 removal patterns. These patterns are provided to convey an understanding of the variety of end results that can be achieved using the devices and methods provided herein. In some scenarios, the patterns can be combined in a single case. Other types of patterns, as well as removal of the full pericardium 22, are also envisioned within the scope of this document.

Figure 2A:
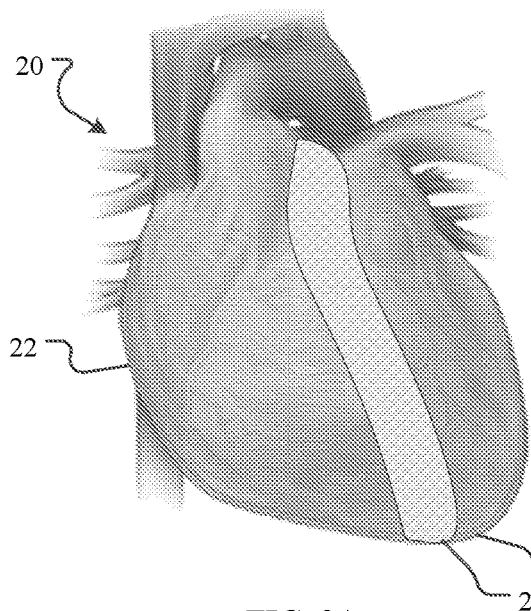
FIGS. 2A-2D are schematic illustrations of a heart after a pericardectomy in accordance with some embodiments provided herein.
Figure 2B:
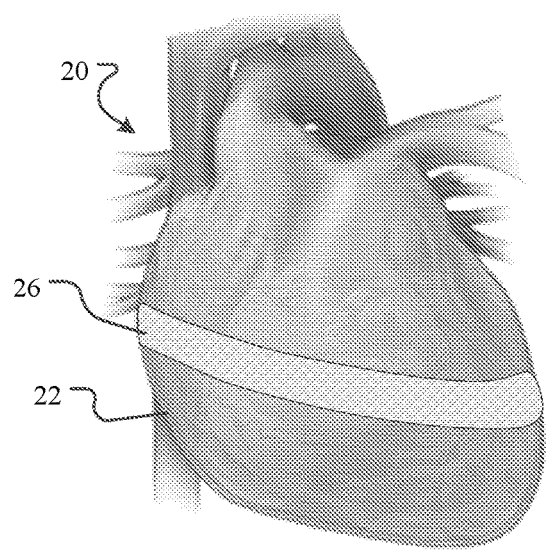

FIGS. 2A and 2B illustrate heart 20 that has had a strip 26 of pericardium 22 removed. The area of strip 26 exposes the epicardial pericardium or the heart tissue (in such cases when the epicardial pericardium has also been removed). Strip 26 of pericardium 22 has been removed using the devices and methods provided herein.

FIG. 2A depicts strip 26 running generally from the apex of heart 20 and in a generally superior/inferior direction. FIG. 2B depicts strip 26 running around the middle of heart 20, and in a generally transverse posterior/anterior direction. In some cases, strip 26 runs all the way around heart 20 (including posterior portions on heart 20 not visible in FIGS. 2A and 2B). In some cases, strip 26 runs partially around heart 20 (e.g., generally as shown, or in a shorter segment than shown). All combinations of directions and lengths of strip 26 are envisioned within the scope of this document.

Measures can be taken to inhibit or prevent the reformation of tissue (e.g., scar tissue) across strip 26. In some cases, the width of strip 26 can be made sufficiently wide to inhibit or prevent the reformation of tissue across strip 26. For example, in some cases making the width of strip 26 from about 0.5 cm to about 1 cm, or about 0.75 cm to about 2 cm or more can inhibit or prevent the reformation of tissue across strip 26. In some cases, the edges of pericardium 22 can be cauterized to inhibit or prevent the reformation of tissue across strip 26. In some cases, the cut edges of pericardium 22 can be doubled over.

In cases where portions of the parietal pericardium are removed but the visceral pericardium remains, measures can be taken to inhibit or prevent attachment of the parietal and visceral pericardial layers that might otherwise create smaller but significant pericardial spaces again, thereby causing restraint in diastole. For example, attachment of the parietal and visceral pericardial layers can be inhibited or prevented by removing a significant amount of the parietal pericardium. In such cases, strip 26 can be made wider to decrease the propensity for attachment of the parietal and visceral pericardial layers.

Figure 2C:
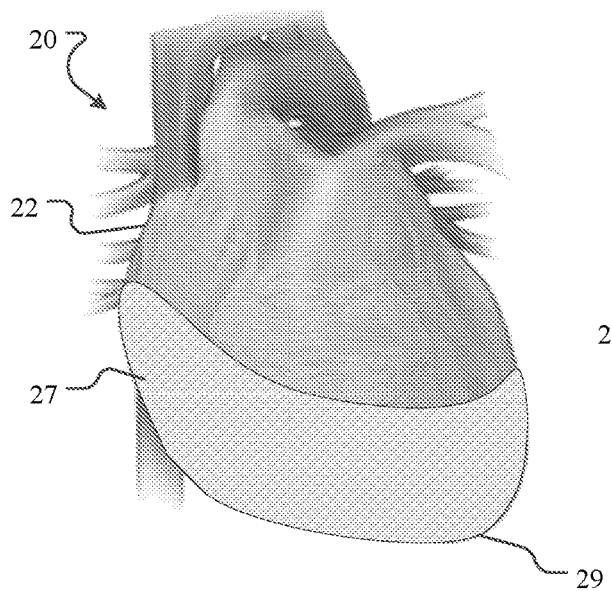

FIG. 2C illustrates another pattern for partial removal of pericardium 22. That is, pericardium from an inferior portion 27 has been removed. The removal can include only the parietal layer, or both the parietal and visceral pericardial layers of pericardium 22.

In some embodiments, the methods of performing pericardectomy provided herein can begin by removing portions of pericardium 22 near the apex 29 of heart 20. For example, a generally circular section of pericardium 22 can be removed at apex 29. In some embodiments, this technique can be used advantageously to avoid the phrenic nerves. If additional removal of pericardium 22 is desired (e.g., if additional diastolic pressure removal is desired), further removal of pericardium 22 can be propagated from the region removed at apex 29. In some embodiments, pericardium 22 covering the left and right ventricles, or substantial portions thereof, are removed.

Figure 2D:
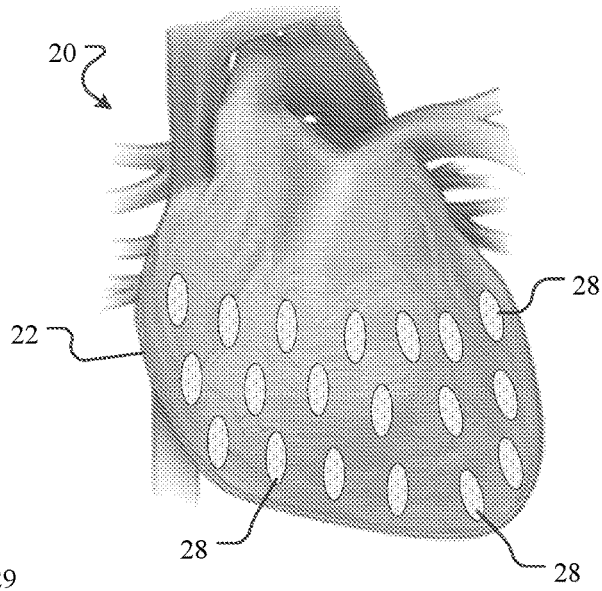

FIG. 2D illustrates another pattern for partial removal of pericardium 22. The pattern is made by creating multiple incisions, tears, or removals of pericardium 22 to create the multiple openings 28. This pattern can allow the volume contained by pericardium 22 to expand. In some embodiments, this method and pattern can be used to relieve pressure within pericardium 22, thereby treating conditions such as HFpFE. The shape of openings 28 can be anything that allows pericardium 22 to expand, e.g., ovals, circles, squares, rectangles, slits and the like. Any suitable quantity of openings 28 can be created. Openings 28 can be located in pericardium 22 anywhere on heart 20 as desired (including posterior regions not shown).

An additional method for partial removal of pericardium 22 can be performed as follows. The pericardial space can be entered by a catheter device, and two small hooks, clamps, or other retention devices (e.g., an Amplatzer-like device) can be installed to the pericardium. A cut to the pericardium can be made, and the catheter device can be positioned between the two small retention devices that were installed in the pericardium. Then the pericardium can be rolled up in a lateral direction by rotary action of the catheter device to create a bundle of pericardium—until a phrenic nerve is reached. The rolling can be stopped as soon as phrenic nerve stimulation is observed. Next, an outer sheath that acts as a cutting tool is placed around the bundle of pericardium. The cutting of the pericardium bundle will remove the pericardium portion and release the catheter device simultaneously.

In some cases, a clamp device can be used to help hold a portion of a pericardium in a region near an entry site. For example, a clamping device configured to be similar to an Amplatzer with larger patches in place of discs can be used to clamp at least a portion of a pericardium. In some cases, the two large patches can be connected between the center of the patches and/or along an outer perimeter of the patches. Once a clamp device is deployed, a user can tug on the clamp device to gain a secure hold on the pericardium and then insert an overtube that can be configured to cut the pericardium. In some cases, a clamp device can be used to enter the pericardium, and then poke back out of the pericardium. In some cases, two different clamp devices can be used at two different sites.

In some cases, a spreader device can be used to help increase a gap within the pericardial space. In some cases, a spreader device can include a number (e.g., 2, 3, 4, 5, 6, or more) expandable petals or blades. Once the spreader device enters the pericardial space with the petals or blades folded along a central axis of the device and positioned in a desired location, a balloon can be inflated such that petals or blades spread apart creating a gap within the pericardial space. In some cases, the balloon can be deflated such that the petals or blades fold along a central axis. In this case, the spreader device can be advanced to another position, and the balloon inflated again, thereby creating additional gaps or openings within the pericardial space. In some cases, one or more petals or blades can included a cutting component or electrodes that can be used to cut tissue as desired.

An additional method for partial removal of pericardium 22 can be performed as follows. The pericardial space can be entered by a catheter device, and two small hooks, clamps, or other retention devices (e.g., an Amplatzer-like device) can be installed to the pericardium. A cut to the pericardium can be made, and the catheter device can be positioned between the two small retention devices that were installed in the pericardium. Then the pericardium can be rolled up in a lateral direction by rotary action of the catheter device to create a bundle of pericardium—until a phrenic nerve is reached. The rolling can be stopped as soon as phrenic nerve stimulation is observed. Next, an outer sheath that acts as a cutting tool is placed around the bundle of pericardium. The cutting of the pericardium bundle will remove the pericardium portion and release the catheter device simultaneously.

Figure 3:
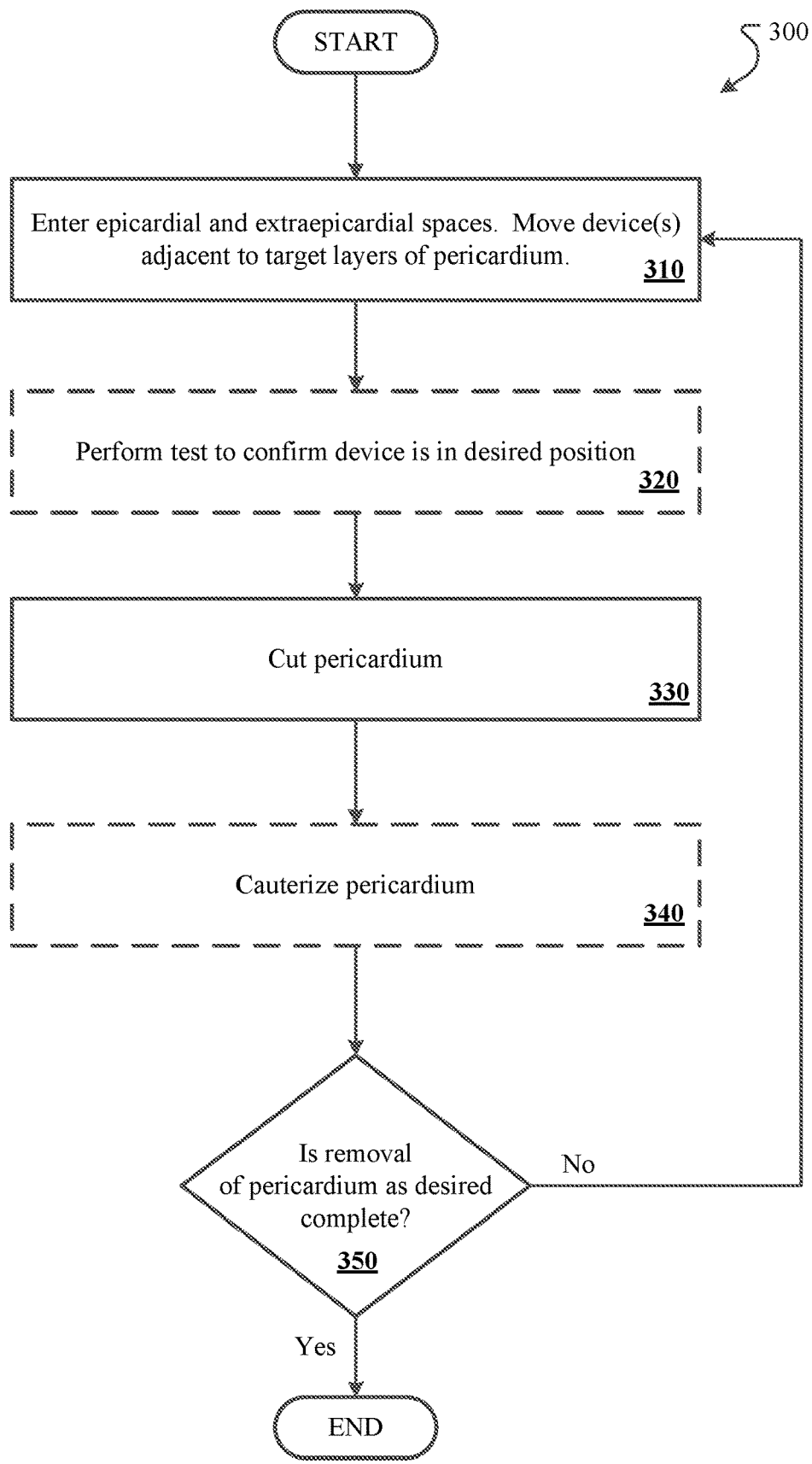
FIG. 3 is flowchart of a pericardectomy method in accordance with some embodiments provided herein.

FIG. 3 is a flowchart of an example embodiment of a method 300 for performing a pericardial modification using the devices provided herein. In general, method 300 can be performed percutaneously or by an open-chest procedure. Method 300 can be used to remove all or a partial portion of one or both pericardial layers. Method 300 can be used to remove pericardium that is diseased, and/or pericardium that is healthy.

At operation 310, a device enters the epicardial and/or extraepicardial spaces and is moved into position adjacent to the pericardium. In some embodiments, a catheter-based device is used. In some embodiments, other types of surgical devices can be used. In some embodiments, a combination of catheter-based devices and other surgical devices can be used. In some embodiments, the device includes grasping and cutting functionality. In some embodiments, a balloon device is included on the device. In some embodiments, sensory functionalities are included on the device, such as Doppler, impedance, and pacing probes to provide a few examples. In some embodiments, a camera device is included on the device. In some embodiments, the device includes electrocautery or cryogenic capabilities. The device may include any combination and subcombination of such functional features, as well as other features that are advantageous for performing pericardectomy procedures.

At operation 320, a test is optionally performed to confirm that the device is in a desired location for cutting the pericardium. For instance, phrenic nerves generally located on the sides of the heart can be advantageously avoided using tests to confirm their location. For example, in some embodiments the device can include a pacing probe to stimulate the area of the tip of the device. If the tip of the device is in the proximity of a phrenic nerve, a movement of the diaphragm may be observed in response to electrical stimulation from the pacing probe. In other cases, other devices such as a Doppler or impedance probe and the like may be optionally used to confirm the device is in a desired location for cutting the pericardium.

In some cases, a device provided herein can be positioned such that the distal end portion is laying adjacent to the targeted layers of the pericardium to be modified to help avoid injuring parts of the mammal's anatomy other than the pericardium. For example, the distal end portion of a cutting device can be positioned to avoid cutting a phrenic nerve, a coronary vessel, or another sensitive structure.

At operation 330, the pericardium is cut, torn, punctured, burned, or otherwise locally destructed to create an opening in the pericardium. In some cases, a cutting device is used to sever the pericardium. In some cases, an electrocautery device can be used to burn an opening in the pericardium. In some cases, other devices including lasers, cryogenic devices, and other cutting tools can be used to create openings in the pericardium.

At operation 340, the edges of pericardium can be optionally cauterized. In some cases, cauterization may beneficially inhibit the reformation of pericardial tissue across the openings created in the pericardium.

At operation 350, the clinician can determine whether the pericardium has been modified as desired, or whether further treatment is desired. When further treatment is desired, for example to make additional cuts in the pericardium to facilitate removal of pericardium, the clinician can generally repeat method 300 until the pericardectomy procedure is complete.

It is usually very fibrous near the sub-xiphoid space. In some cases, the methods provided herein can include entering into the pericardium near the sub-xiphoid access point and then exiting once the device progresses past the fibrous area. For example, a device provided herein can include a small hypotube that has a hollow needle within it. A wire can be positioned within the hollow needle. A distal end region of the wire can include an electrode with RF to help pierce through the tissue.

In some cases, a method provided herein can be performed in a manner that reduces bleeding and/or pain during and/or after the procedure. For example, a pericardial sheath can be used that is coated with an agent that acts as a sponge (e.g., a chemical sponge) to soak up blood and/or prevent bleeding. In some cases, the agent can be a thrombostatic agent. Examples of coating agents include, without limitation, gelfoam (purified porcine skin gelatin), human thrombin, and bovine thrombin. In some cases, an RF catheter of a device provided herein can be configured to elute a steroid, depo-medrone, ionized lidocaine, lidocaine, and/or bupivacaine. Removing the pericardium itself can help reduce post-procedural pain because the pain fibers are being removed along with it. In some cases, removal of the pericardium can become adjunct to other procedures (e.g., left atrial appendage closure or intractable angina treatment) to reduce pain. If some of the pericardium is left behind, however, (for example, areas near the phrenic nerve), low DC energy can be delivered to reduce pain fibers. Such energy can be delivered as described herein.

In some embodiments, the pericardial modification devices and methods provided herein involve modification of the pericardium rather than pericardectomy. Such modification techniques can have value in actually keeping the pericardial space and structures intact but greatly minimizing pericardial restraint. One example pericardial modification procedure can be performed as follows.

First, a balloon device can be positioned in the pericardial space. The balloon device can include electrodes on at least one of the balloon's surfaces. Some electrodes can be orientated so they are pointed toward the pericardial space. Then, those electrode are stimulated for the purposes of mapping the course of the phrenic nerve. Those electrodes are then taken away from the energy delivering circuit with a switching system.

Other electrodes on the balloon are then used to deliver energy to the parietal pericardium. The energy could be radiofrequency ("RF"), ultrasound, or DC current at either electroporative or ablation dose levels. In some embodiments, the balloon itself can be differentially expandable. That is, the balloon can expand so as to exert substantial pressure against the parietal pericardial surface, but only minimal pressure towards the surface of the heart, to avoid coronary compression. This pericardial modification method can provide a combination of parietal pericardium dilation, breaking of the fibrous pericardium, and DC/RF softening of the pericardium (which in turn allows more dilation).

In some cases, the methods and devices provided herein can be used to access the pericardium using a mediastinal approach, a pericardial window, and/or an open pericardial access approach, for example, when some other surgery is being performed or contemplated. In some cases, the methods and devices provided herein can be used to access the pericardium from the heart itself. For example, the methods and devices provided herein can be used to exit the heart, suction in or grasp at least a portion of the pericardium, and remove it via an endocardial approach. In such cases, a closure device can be positioned in the exit site of the heart once the procedure is completed.

In some cases, the methods and devices provided herein can be used to cut or modify the pericardium without extracting the pericardium. For example, once cut or modified, the pericardium can be left in the space in a manner where it can no longer impede myocardial relaxation.

In some cases, a stimulation device can be used to control the phrenic nerve. For example, a sub-threshold stimulation device can be used to improve diaphragmatic function in patients with diaphragmatic problems. Stimulating the phrenic nerve in a synchronous manner with the cardiac cycle can be performed. For example, a wire placed on both phrenic nerves for cross-shunting purposes can be used to treat unilateral phrenic palsy. In some cases, electrodes can be placed on the phrenic nerve on both sides, and a central wire can be used as a shunt between the two of them. In these cases, if one phrenic nerve is paretic, then the impulse from the other phrenic nerve can be shunted down towards the diaphragm.

FIGS. 4-7 illustrate additional devices that can be used to perform the pericardial modification techniques provided herein. It should be understood that the features included in one device embodiment can be combined with features from other device embodiments to create hybrid devices. For example, an electrocautery feature depicted on one device can be used on another device whether or not such an electrocautery feature is depicted on the other device. All other features can be similarly used in any of the devices whether or not the particular figure includes such features.

Figure 4:
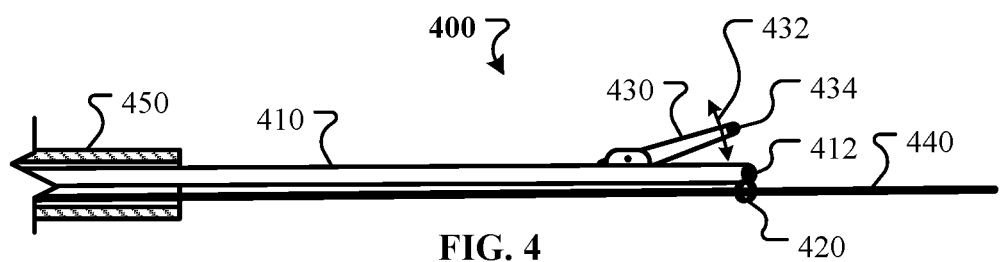
FIG. 4 illustrates another pericardial modification device in accordance with some embodiments provided herein.
Figure 6:
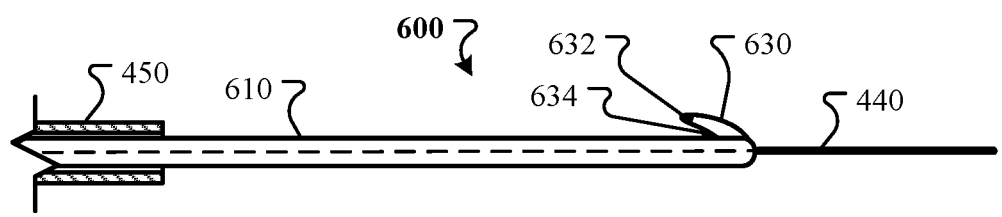
FIG. 6 illustrates another pericardial modification device in accordance with some embodiments provided herein.

FIG. 4 illustrates another example pericardial modification device 400. Pericardial modification device 400 includes a shaft 410, a collar 420, and an incisor 430. In some implementations, pericardial modification device 400 is used with a guidewire 440 and an introducer sheath 450 (shown in longitudinal cross-section). Collar 420 is coupled to shaft 410. In some embodiments, collar 420 is coupled to a distal end portion of shaft 410. Collar 420 defines a central opening in which guidewire 440 can be slidably received. The distal end of pericardial modification device 400 includes an atraumatic tip. In some embodiments, pericardial modification device 400 is steerable. In alternative embodiments, shaft 410 can include a lumen which can slidably receive guidewire 440 (as shown in FIG. 6, for example). In some such embodiments, collar 420 is omitted.

In some embodiments, incisor 430 is pivotably coupled to shaft 410. Incisor 430 can be pivoted as indicated by arrow 432. Such pivoting action can be initiated by a clinician operator at a handle portion exterior to the patient (e.g., refer to FIG. 1A). The pivoting action allows incisor 430 to perform as a scissors in combination with shaft 410 to facilitate incising tissue such as the pericardium. In some embodiments, shaft 410 includes a portion that is complementary to incisor 430 so that an efficient shearing action is achieved. In some embodiments, incisor 430, or shaft 410, or both, may include one or more electrocautery electrodes to facilitate modification of the pericardium and/or cauterization of tissue. In some embodiments, pericardectomy device 400 can also include nerve stimulation capabilities to assist with identification of nerve locations.

In some embodiments, incisor 430 and/or shaft 410 may include one or more electrodes 434 and 412 respectively to assist with nerve identification. For example, in some implementations electrodes 434 and/or 412 may be useful for identification of the location of phrenic nerves and other nerves. Alternatively, or additionally, electrodes 434 and 412 may be used to sense electrical signals from the left atrial appendage and/or other sources of electrical signals.

Figure 5:
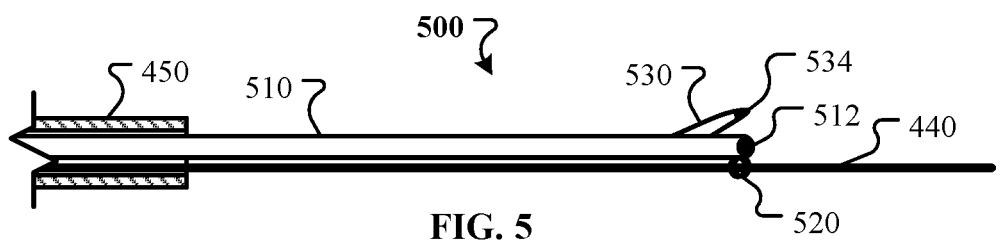
FIG. 5 illustrates another pericardial modification device in accordance with some embodiments provided herein.

FIG. 5 illustrates another example pericardial modification device 500. Pericardial modification device 500 is a forward-cutting device. Pericardial modification device 500 includes a shaft 510, a collar 520, and an incisor 530. In some implementations, pericardial modification device 500 is used with a guidewire 440 and an introducer sheath 450. Collar 520 is coupled to shaft 510. In some embodiments, collar 520 is coupled to a distal end portion of shaft 510. Collar 520 defines a central opening in which guidewire 440 can be slidably received. In alternative embodiments, shaft 510 can include a lumen which can slidably receive guidewire 440 (as shown in FIG. 6, for example). In some such embodiments, collar 520 is omitted.

Incisor 530 is coupled to shaft 510. In some embodiments, incisor 530 is fixedly coupled to shaft 510. In some embodiments, incisor 530 is pivotably coupled to shaft 510. For example, in some embodiments incisor 530 is pivotable in relation to shaft 510 and spring-biased to pivot outward to the configuration as shown. However, when incisor 530 is located within sheath 450, incisor 530 can be pivoted closer to shaft 510 to provide a lower profile. In some embodiments, upon emergence from sheath 450, spring-biased incisor 530 can self-pivot outward from shaft 510 to the configuration as shown. Incisor 530 can include one or more sharp edges. In some embodiments, incisor 530 includes a sharp tip that can penetrate tissue such as the pericardium. In some embodiments, incisor 530, or shaft 510, or both, may include one or more electrocautery electrodes to facilitate modification of the pericardium and/or cauterization of tissue. In some embodiments, pericardectomy device 500 can also include nerve stimulation capabilities to assist with identification of nerve locations. In some embodiments, pericardial modification device 500 is steerable.

In some embodiments, incisor 530 and/or shaft 510 may include one or more electrodes 534 and 512 respectively to assist with nerve identification. For example, in some implementations electrodes 534 and/or 512 may be useful for identification of the location of phrenic nerves and other nerves. Alternatively, or additionally, electrodes 534 and 512 may be used to sense electrical signals from the left atrial appendage and/or other sources of electrical signals.

FIG. 6 illustrates another example pericardial modification device 600. Pericardial modification device 600 is a reverse-cutting device. Pericardial modification device 600 includes a shaft 610 and an incisor 630. In some implementations, pericardial modification device 600 is used with a guidewire 440 and an introducer sheath 450. In the depicted embodiment, shaft 610 defines a central lumen in which guidewire 440 can be slidably received. In some alternative embodiments, a collar can be used to couple with guidewire 440 rather than, or in addition to, the central lumen in shaft 610. The distal end of pericardectomy device 600 includes an atraumatic tip. In some embodiments, pericardial modification device 600 is steerable. For example, in some embodiments the distal tip portion of pericardial modification device 600 is steerable. In some such embodiments, steerage of the distal tip portion of pericardial modification device 600 can be used to create a tent in the pericardium. Thereafter, a wire can be made to emerge from the distal tip portion of pericardial modification device 600 such that the wire can pierce the pericardial tissue. In some embodiments, the wire is an electrocautery wire and the wire can be used to sever the pericardial tissue after the puncture is made. In some embodiments, incisor 630 can be used to sever the pericardial tissue after the puncture is made.

Incisor 630 includes a tip 632 and a cutting portion 634. In some embodiments, tip 632 and/or cutting portion 634 are sharpened to enable piercing and/or shearing of tissue, such as pericardial tissue. In some embodiments, tip 632 and/or cutting portion 634 are electrocautery electrodes that can separate and/or cauterize tissue, such as pericardial tissue. In some embodiments, pericardial modification device 600 can also include nerve stimulation capabilities to assist with identification of nerve locations. In some embodiments, pericardial modification device 600 is steerable.

Figure 7:
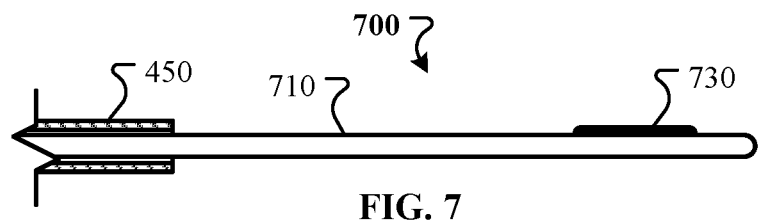
FIG. 7 illustrates another pericardial modification device in accordance with some embodiments provided herein.

FIG. 7 illustrates another example pericardial modification device 700. Pericardial modification device 700 includes a shaft 710 and an electrocautery portion 730 that is disposed near the distal end portion of shaft 710. The distal end of pericardial modification device 700 includes an atraumatic tip. Electrocautery portion 730 can be used to separate and/or cauterize tissue, such as pericardial tissue. Shaft 710 can be steerable in some embodiments. Shaft 710 can be flexible in some embodiments.

Pericardial modification device 700 can also include aspects that assist a clinician to determine an orientation of electrocautery portion 730, so that electrocautery portion 730 can be positioned against the tissue to be severed. To accomplish that, in some embodiments a sensing electrode (not shown) can be included on shaft 710. The sensing electrode can be disposed on side of shaft 710 that is opposite from electrocautery portion 730. The sensing electrode can be used to sense electrical signals from the surface of the heart. When the sensing electrode detects such signals, it can be deduced that electrocautery portion 730 is positioned opposite of the surface of the heart and, hence, against the pericardial tissue as desired. In some embodiments, fluoroscopy can be used to visualize the orientation of electrocautery portion 730. In some such embodiments, one or more radiopaque markers can be included on shaft 710 to facilitate such visualization of the orientation of electrocautery portion 730 in relation to the surface of the heart and the pericardium.

FIGS. 8A-8F are a series of illustrations depicting a pericardial modification procedure in accordance with some embodiments provided herein. The pericardial modification procedure is performed using an exemplary pericardectomy system 800 on a heart 20 that has a pericardium 22. Pericardectomy system 800 represents any of the example pericardectomy devices and systems provided herein, and/or combinations thereof. For example, while pericardectomy system 800 does not illustrate a grasping device for grasping and manipulating the pericardial tissue, one or more grasping devices may be included in some embodiments. It should also be understood that while FIGS. 8A-8F show the incision and removal of a particular portion of pericardial tissue (orientated on a particular portion of heart 20), other portions and locations of pericardial tissue can be incised and/or removed using the same or similar pericardial modification procedure techniques as illustrated here. For example, in another example implementation the pericardial tissue constraining the apex of heart 20 can be modified by, for example, by incision and/or removal (refer also to FIGS. 2A-2D for additional examples). The pericardial modification procedure is performed while avoiding trauma to the epicardial surface of heart 20 as well as the phrenic nerves.

Figure 8C:
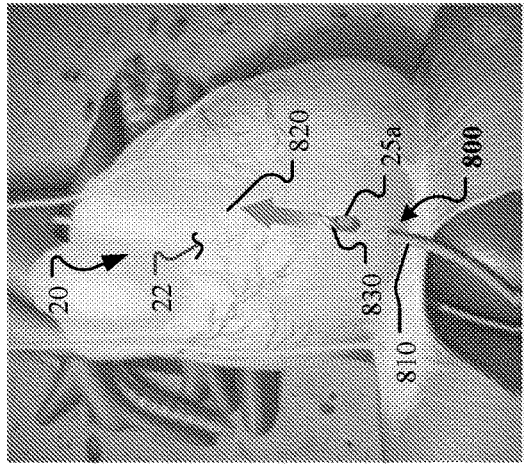
FIGS. 8A-8F are a series of illustrations depicting a pericardial modification procedure in accordance with some embodiments provided herein.
Figure 8F:
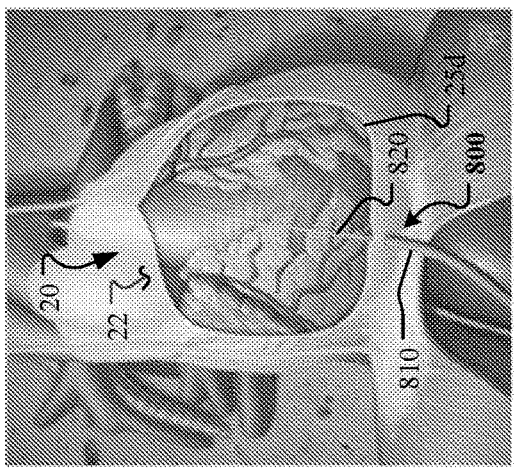
Figure 8B:
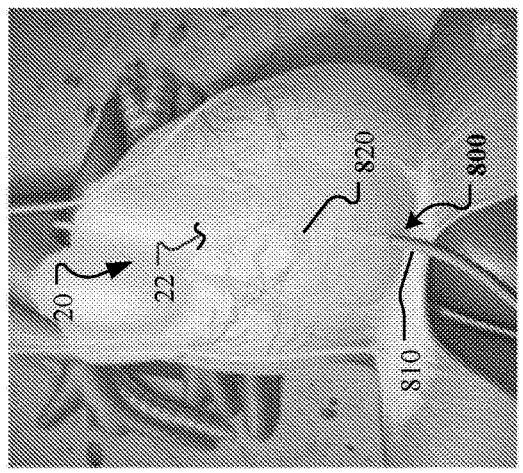
Figure 8E:
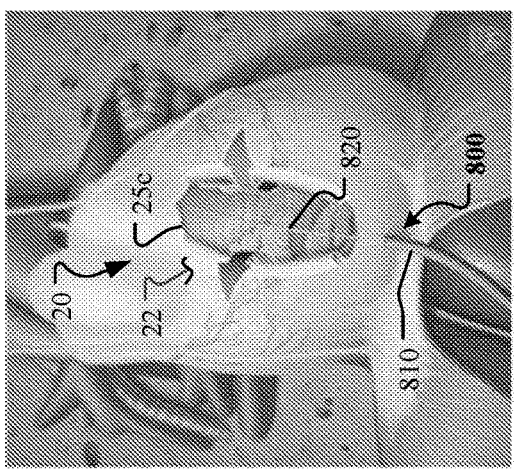
Figure 8A:
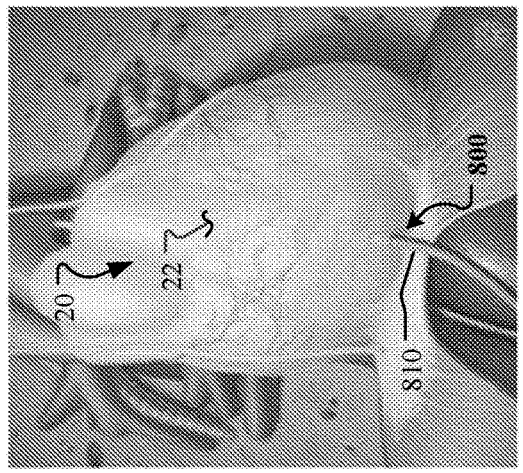
Figure 8D:
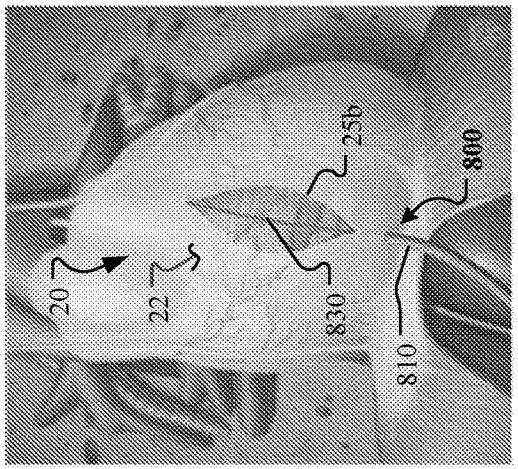

In FIG. 8A, a delivery sheath 810 of pericardectomy system 800 is shown after having been partially inserted through an incision to pericardium 22. In this orientation, the distal tip portion of delivery sheath 810 is within the pericardial sack and adjacent to the surface of heart 20.

In FIG. 8B, a guidewire 820 has been advanced from sheath 810. Advancement of guidewire 820 can be performed using fluoroscopy or other imaging modalities.

In FIGS. 8C and 8B, a pericardial modification device 830 is being advanced over guidewire 820. Pericardial modification device 830 is creating an opening 25a and 25b in pericardium 22.

Figure 9:
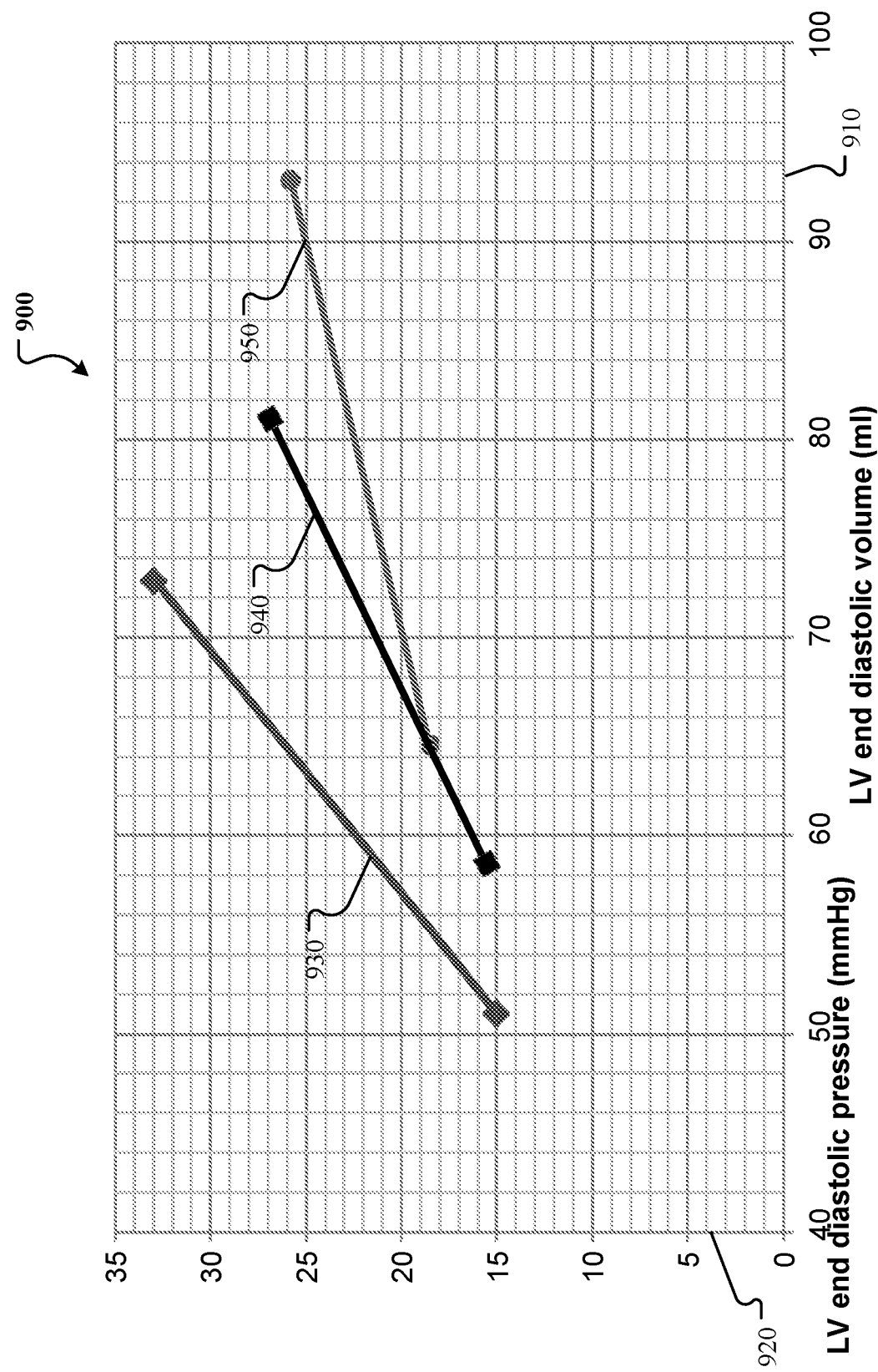
FIG. 9 is a graph that illustrates the results of a pericardial modification procedure.

In FIGS. 8E and 8F, pericardial modification device 830 has been retracted into sheath 810. The openings 25c and 25d in pericardium 22 are enlarged as desired. In some embodiments, an additional grasping/cutting device is used to remove the pericardial tissue to arrive at the configuration shown in FIG. 8F With reference to FIG. 9, a graph 900 of left ventricular end diastolic volume 910 (on the x-axis) versus left ventricular end diastolic pressure 920 (on the y-axis) is provided. The lines 930, 940, and 950 are the results from acute experiments using four normal dogs. These experiments were performed to verify the acute benefits of pericardiectomy, and to explore whether a limited pericardial incision might provide similar benefit to complete pericardial resection. Left ventricular pressures and volumes were measured at baseline (the lower endpoint of each line 930, 940, and 950) and after rapid saline loading (the upper endpoint of each line 930, 940, and 950). Line 930 shows the left ventricular pressure and volume with the pericardium intact. Line 940 shows the left ventricular pressure and volume after a single linear left lateral pericardial incision. Line 950 shows the left ventricular pressure and volume after complete pericardiectomy.

It can be seen that the left ventricular diastolic pressure-volume relation shifted rightward indicating improved compliance with performance of the pericardial modification procedure techniques provided herein. A significant amount of this benefit was achieved with the single linear incision over the left lateral pericardium as represented by line 940. Note that the magnitude of increase in left ventricular filling pressures with saline bolus (700 ml) was lower from thoracotomy to pericardial incision to full pericardiectomy. There was a slight creep upward in left ventricular end diastolic pressures at the re-baseline state prior to the final saline loading (after full pericardiectomy), likely due to the additive effect of receiving multiple serial boluses to increase circulating plasma volume. Overall, the increase in left ventricular pressure per increase in left ventricular volume with saline load decreased progressively from line 930 with the pericardium intact (0.90±0.22 mmHg/ml) to line 940 with the pericardial incision (0.44±0.13, p=0.04 vs. intact) to line 950 with the full pericardiectomy (0.28±0.24, p=0.006 vs. intact, p=0.3 vs. incision).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for treating a heart of a patient, the method comprising:
    creating a puncture in a parietal layer, and only in the parietal layer, of a pericardium of the patient;
    inserting a guidewire through the puncture and to within a pericardial sac;
    advancing a delivery sheath over the guidewire and to within the pericardial sac;
    advancing a pericardial modification device through the delivery sheath to position an incisor of the pericardial modification device within the pericardial sac;
    creating a tent of pericardial tissue using the pericardial modification device to force the pericardium away from the heart of the patient; and
    cutting, using the incisor of the pericardial modification device, an elongate incision in the parietal layer, and only in the parietal layer.

2. The method of claim 1, wherein using the incisor of the pericardial modification device to create the elongate incision in the parietal layer comprises puncturing an inner wall of the parietal layer that is in contact with a pericardial fluid and through an outer wall of the parietal layer.

3. The method of claim 2, further comprising using a sharp tip of the incisor to initiate the cutting of the elongate incision in the parietal layer.

4. The method of claim 1, wherein the incisor is pivotably coupled to a shaft of the pericardial modification device.

5. The method of claim 1, wherein a distal tip portion of a shaft of the pericardial modification device is steerable, and wherein the tent of pericardial tissue is created using steerage of the distal tip portion of the shaft.

6. The method of claim 5, wherein the puncture in the parietal layer is created near a subxiphoid access point of the patient.

7. The method of claim 1, further comprising, after creating the tent of pericardial tissue, actuating the incisor of the pericardial modification device using a handle of the pericardial modification device.

8. The method of claim 1, further comprising relieving pressure exerted by the pericardium on the heart as a result of creating the elongate incision.

9. The method of claim 1, further comprising, prior to cutting the elongate incision, identifying a location of a phrenic nerve.

10. The method of claim 9, wherein an electrode of the pericardial modification device is used to identify the location of the phrenic nerve.

11. The method of claim 9, wherein two electrodes of the pericardial modification device are used to identify the location of the phrenic nerve.

12. The method of claim 9, further comprising, after identifying the location of the phrenic nerve and prior to cutting the elongate incision, moving the pericardial modification device away from the location of the phrenic nerve.

13. The method of claim 9, further comprising, detaching the phrenic nerve from the parietal layer after identifying the location of the phrenic nerve.

14. The method of claim 1, further comprising delivering a contrast agent into the pericardium.

15. The method of claim 14, wherein the contrast agent stains the pericardial tissue.

16. The method of claim 1, wherein using the pericardial modification device to create the elongate incision comprises deploying a blade of the pericardial modification device to puncture only the parietal layer.

17. The method of claim 16, further comprising, with the blade remaining deployed, creating the elongate incision in the parietal layer, and only in the parietal layer, from within the pericardial sac.

18. The method of claim 1, wherein the elongate incision is created longitudinally, extending over a right ventricle or a left ventricle.

* * * * *